Figure 1:
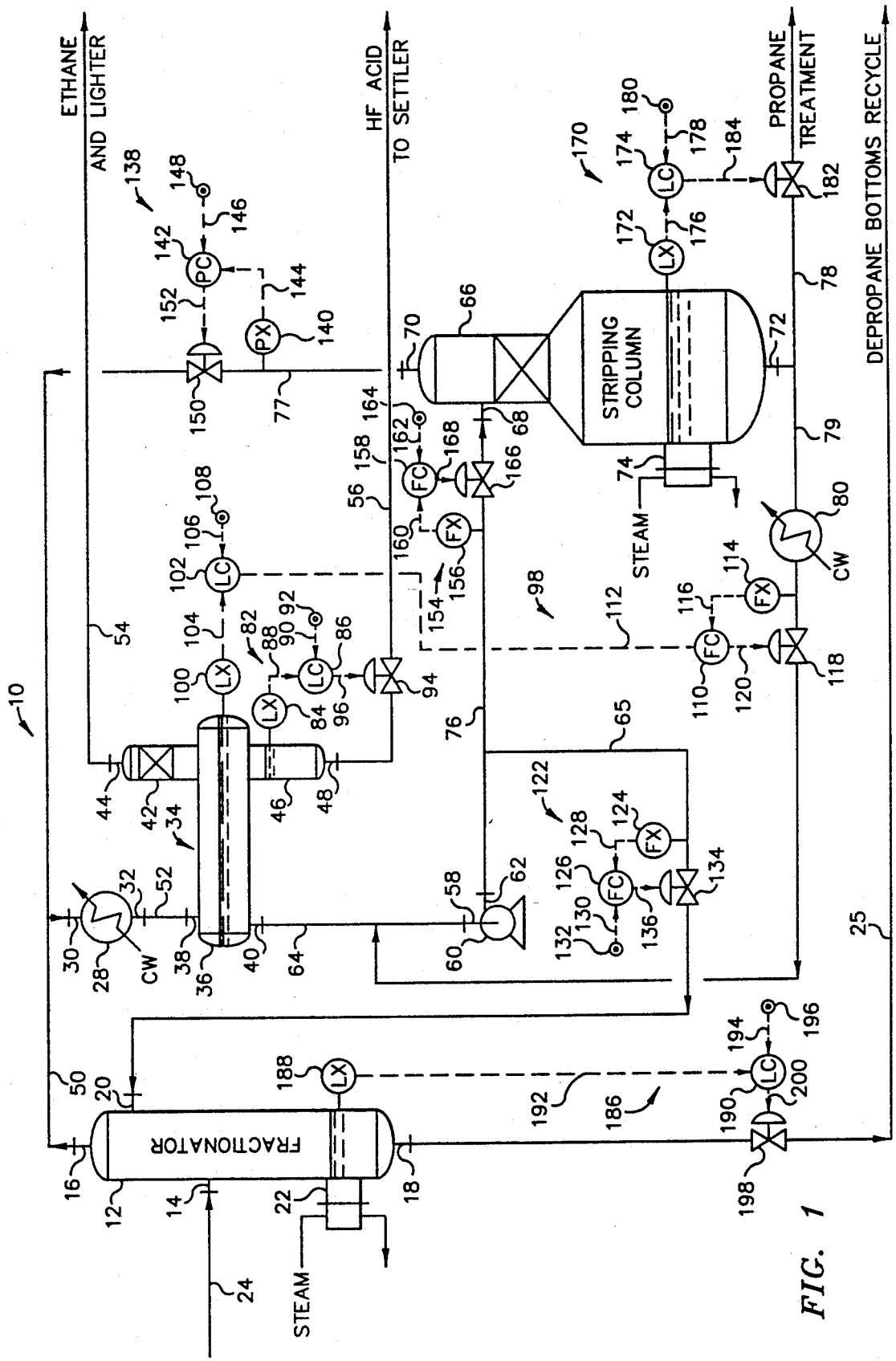

United States Patent [19]

Hovis et al.

[11] Patent Number: 5,252,295

[45] Date of Patent: Oct. 12, 1993

[54] CONTROL OF HF ALKYLATION PROPANE STRIPPER

[75] Inventors: Keith W. Hovis; Henry K. Hachmuth, both of Bartlesville, Okla.; Michael L. Gray, Spartanburg, S.C.

[73] Assignee: Phillips Petroleum Company, Bartlesville, Okla.

[21] Appl. No.: 891,146

[22] Filed: Jun. 1, 1992

Related U.S. Application Data

[62] Division of Ser. No. 676,030, Mar. 27, 1991.

[51] Int. Cl.$^5$ .............................................. G05D 9/00
[52] U.S. Cl. .................................. 422/106; 422/108; 422/110
[58] Field of Search .............. 422/106, 108, 110, 111; 585/701, 710, 719, 723, 956

[56] References Cited

U.S. PATENT DOCUMENTS

| | | | |
|---|---|---|---|
| 3,763,265 | 10/1973 | Hutson et al. | 260/683.42 |
| 3,929,925 | 12/1975 | Chapman | 585/723 |
| 4,182,924 | 1/1980 | Chapman | 585/712 |
| 4,182,925 | 1/1980 | Chapman | 585/719 |
| 4,199,409 | 4/1980 | Skraba | 203/39 |
| 4,212,889 | 7/1980 | Fuentevilla | 422/106 |
| 4,224,283 | 9/1980 | Potts | 422/111 |
| 4,237,093 | 12/1980 | McCoy | 422/106 |
| 4,366,120 | 12/1982 | Cowley | 422/106 |
| 4,925,635 | 5/1990 | Hampton | 422/106 |

OTHER PUBLICATIONS

A. K. Schmidt and H. L. List. *Material and Energy Balances*, pp. 31-34, Prentice-Hall, Inc., Englewood Cliffs, N.J., 1962.

*Primary Examiner*—Robert J. Warden
*Assistant Examiner*—Hien Tran
*Attorney, Agent, or Firm*—Charles W. Stewart

[57] ABSTRACT

A process and apparatus for recovering propane product from HF alkylation process that is substantially free of HF acid. The invention allows for the improvement in the operation of an HF alkylation propane stripper by utilizing a bottoms recycle stream.

8 Claims, 1 Drawing Sheet

CONTROL OF HF ALKYLATION PROPANE STRIPPER

This application is a division of application Ser. No. 07/676,030, filed Mar. 27, 1991, now allowed.

This invention relates to an HF alkylation process and the efficient recovery of hydrocarbon product.

In the HF alkylation process, hydrocarbon products can be produced by alkylation reactions involving the combination of isoparaffins having low boiling temperatures such as isobutane with olefins having low boiling temperatures such as ethylene, propylene, butene, pentene and the like in the presence of HF acid catalyst. In the typical HF alkylation process, hydrocarbon feed primarily comprising C3 to C6 olefins with limited quantities of propane and lighter compounds are mixed with a butane mixture of isobutane and n-butane. This hydrocarbon mixture is reacted in the presence of HF acid catalyst to form a hydrocarbon mixture of high octane alkylate along with unreacted isoparaffins, normal paraffins, light hydrocarbons, including propane and ethane, and HF acid. The reaction product mixture must subsequently undergo a phase separation of the HF acid and the hydrocarbon with the hydrocarbon phase further undergoing fractionation to separately recover the products of alkylate, propane and normal butane.

The amount of propane produced in an HF alkylation process can vary substantially depending upon the process feed composition and the alkylation reactions which take place. In particular, there are two primary factors which determine the amount of propane recovered in the HF alkylation process. The first factor being the amount of propane actually charged to the unit which can vary upwardly to twenty percent or more of the hydrocarbon feed. The other factor having a bearing upon the amount of propane produced is related to the quantity of the olefin propylene introduced into the process unit and the extent to which the hydrogen transfer reaction takes place. In the hydrogen transfer reaction, as much as twenty percent of the propylene can be converted to propane by reacting propylene with HF acid to form the hydrogen saturated compound of propane. In many alkylation processes, as much as thirty percent of the olefin charge can be propylene.

The potentially wide variability of propane processed in an alkylation unit can pose operating problems in the various pieces of fractionation equipment. In a common process, the separated hydrocarbon alkylation product is charged to a fractionation section where alkylate, unreacted paraffin, isoparaffins, and propane and lighter hydrocarbons are recovered. Typically, the overhead of a fractionation column comprising essentially propane and lighter hydrocarbons and contaminating quantities of HF acid is charged to a propane stripping column where a portion of the propane and essentially all the light hydrocarbons and HF acid is driven overhead, and the remaining portion of propane and essentially all heavier hydrocarbons are recovered as a bottoms product. The bottoms product is essentially free of HF acid, but requires further treatment to remove any remaining traces of HF acid, fluoride compounds, and other contaminants prior to storage and sales. Many operating problems occur in the propane stripper in which an essentially on-specification propane product is produced.

In designing an alkylation process, the propane stripper must be designed and sized to accommodate the situations of maximum propane production, or at least, it should be designed to handle the typical case of propane production. But, occasionally during operation there are dramatic changes in feedstock composition resulting in substantial reductions in the quantity of propane produced and processed in the alkylation unit. This reduction in propane production consequently results in a large reduction in the charge rate to the propane stripper, which has earlier been designed for a much greater charge rate. The reduced charge rate has a negative effect upon the operation of the propane stripper by making it more difficult to control. Because of the difficulty in the control of the HF stripper at lower charges rates, off-specification propane product is often make resulting in the further contamination of products and in the transfer of HF acid to other propane treatment vessels where additional hazards are created.

I have discovered a method and an apparatus for improving the ease and efficiency of operation of the propane stripper within an HF alkylation process at low charge rates.

Accordingly, it is an objective of this invention to provide an improved alkylation process.

Another object of this invention is to reduce the energy costs associated with the operation of an HF alkylation fractionation system.

A further object of this invention is to improve the operating safety of an HF alkylation process.

A still further object of this invention is to provide for the ability to handle a wide variance in alkylation process feed composition.

Other objects, aspects, and features of the present invention will be evident from the following detailed description of the invention, the claims and the drawing in which:

FIG. 1 is a schematic diagram illustrating a preferred embodiment of the present invention.

A hydrocarbon effluent is taken from the phase separator in which the alkylation hydrocarbon product is separated from the alkylation catalyst and is charged to a fractionator. Typically, the fractionator serves as a depropanizer where the overhead contains essentially propane and light hydrocarbons, and the bottom product contains essentially hydrocarbons which are heavier than propane. This process is often described as being a split-flow process with a portion of the phase separator hydrocarbon effluent along with the depropanizer bottoms being charged to a stripper fractionator where the alkylate product is separated from butanes and lighter hydrocarbons and is recycled to the alkylation reactor. An alternative approach to processing phase separator effluent is to charge it to a main fractionator by which an alkylate product is separated from butane and lighter hydrocarbons. The butane and lighter hydrocarbons are passed to a depropanizer where a separation between propane and lighter and butane and heavier is made. The propane and lighter stream is condensed and accumulates in an overhead phase separator where hydrocarbon and certain quantities of HF acid is separated. The hydrocarbon, which is saturated with HF acid, is charged to a propane stripper where propane and heavier compounds are separated from HF acid, ethane and lighter compounds.

What often happens in the operation of an HF alkylation process is that the amount of propane produced is significantly lowered through a change in the quantity of either propane or propylene, or both, being fed to the process. This reduction in the charge rate of propane and propane precursors consequently results in a proportional reduction in the amount propane feed available to the propane stripper. When the feed rate to the propane stripper is significantly reduced, it becomes increasingly more difficult to efficiently and easily control the oepration of the fractionator. As an embodiment of ths invention, provision is made to recycle propane stripper bottoms to the feed of the propane stripper in order to maintain a large enough feed rate which will allow better control of the fractionator. The amount of bottoms recycle is determined by measuring the depropanizer overhead accumulator level and adjusting the recycle flow to maintain a desired accumulator level. For example, if the accumulator level is measured to be below the desired level, then the bottoms recycle flow rate is increased until the accumulator level is returned to the desired level. Altnernatively, if the measured level exceeds that desired, then the recycle flow is reduced until the desired level is reached. The ability to adjust the propane stripper bottoms recycle in response to changes in accumulator level allows for a fixed propane stripper charge rate which further results in an improved operation.

Included as possible elements of a preferred embodiment of the invention are a number of control schemes which are shown in FIG. 1. The invention, however, can include other different types of control configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

The controllers shown may utilize the various modes of control such as proportional, proportional-integral, proportional-derivative, or proportional-integral-derivative. In this preferred embodiment, proportional-integral-derivative controllers are utilized but any controller capable to accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so than an output signal having a voltage level of 5.0 volts corresponds to 50 percent, some specified flow rate, or some specified temperatures.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signals handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to FIG. 1, there is illustrated propane stripping system 10 that is a part of an HF alkylation process system. At the front-end of propane stripping system 10 is fractionator 12 that is provided with feed inlet 14, bottoms outlet 18, and reflux inlet 20. As a further part of fractionator 12 is reboiler 22, which is operably connected to the bottom of fractionator 12, for providing the reboil heat or heat energy necessary to operate fractionator 12. Operably connected to feed inlet 14 is conduit 24 for conveying fluid to fractionator 12. Conduit 25 is operably connected to bottoms outlet 18 for conveying fluid from fractionator 12 for further downstream processing (not shown).

In the overhead system of fractionator 12 is condenser 28, having a condenser inlet 30 and condenser outlet 32, overhead accumulator 34 comprising a medial section 36, which is provided with accumulator inlet 38 and medial section outlet 40, a top section 42, which is provided with a top section outlet 44, and bottom section 46, which is provided with a bottom section outlet 48. Medial section outlet 40 is operably connected to medial section 36 in such a manner as to provide for fluid flow communication and for conveying fluid away from medial section 36. Bottom section outlet 48 is operably connected to bottom section 46 in such a manner as to provide for fluid flow communication and for conveying fluid away from bottom section 46. Providing for fluid flow communication between fractionator 12 and condenser 28 is conduit 50, which is operably connected between overhead outlet 16 and condenser inlet 30, for conveying fluid from fractionator 12 and condenser 28. Conduit 52 is operably connected between condenser outlet 32 and accumulator inlet 38 for conveying fluid from condenser 28 to overhead accumulator 34.

For removing gaseous fluid from top section 42 of overhead accumulator 34, there is provided conduit 54, which is operably connected to top section outlet 44, for conveying fluid from top section 42 to downstream processing (not shown). Conduit 56 is operably connected to bottom section outlet 48 for conveying liquid fluid from bottom section 46 to an HF acid settler vessel (not shown) of the HF alkylation process system. Operably connected between medial section outlet 40 and suction inlet 58 of pump 60, having suction inlet 58 and discharge outlet 62, is conduit 64 for conveying fluid from medial section 36 to pump 60. Providing for an overhead reflux to fractionator 12 is conduit 65, which is operably connected between discharge outlet 62 and reflux inlet 20, for conveying fluid from pump 60 to fractionator 12.

For receiving a fluid stream from overhead accumulator 34 is stripping column 66 having inlet 68, overhead outlet 70 and bottoms outlet 72. Stripping column 66 is further provided with reboiler 74, which is operably connected to the bottom of stripping column 66, for providing the reboil heat or heat energy necessary to operate stripping column 66. Operably connected between discharge outlet 62 and inlet 68 is conduit 76 for conveying fluid from pump 60 to stripping column 66. For conveying a gaseous fluid from stripping column 66 to condenser 28 is conduit 77 that is operably connected between overhead outlet 70 and condenser inlet 30. Operably connected to bottoms outlet 72 is conduit 78 for conveying fluid from stripping column 66 for further downstream treating (not shown). For recycling fluid from stripping column 66 to suction inlet 58 is conduit 79 that is operably connected between bottoms outlet 72 and suction inlet 58. Optionally, heat exchanger or cooler 80 can be interposed in conduit 79.

To control the fluid level within bottom section 46 is a level control system 82. In level control system 82, there is provided level sensor 84, which is operably located in bottom section 46, for sensing the fluid level within bottom section 46. For transmitting a first input signal to level controller 86 is signal line 88 that is operably connected between level sensor 84 and level controller 86. For transmitting a second input signal to level controller 86 is signal line 90 that is operably connected between a manual input signal switch 92 and level controller 86. Operably connected between level controller 86 and control valve 94, which is interposed in conduit 56, is signal line 96 for transmitting an output signal from level controller 86 to control valve 94.

To control the fluid level within medial section 36 is a level control system 98. Provided in level control system 98 is level sensor 100, which is operably located in medial section 36, for sensing the fluid level medial section 36. For transmitting a first input signal to level controller 102 is signal line 104 that is operably connected between level sensor 100 and level controller 102. For transmitting a second input signal to level controller 102 is signal line 106 that is operably connected between manual input signal switch 108 and level controller 102. For transmitting an output signal from level controller 102 as a first input signal to flow controller 110 is signal line 112 that is operably connected between level controller 102 and flow controller 110. Operably located in conduit 79 is flow sensor 114 for sensing the fluid flow rate of the fluid passing through conduit 79. Operably connected between flow sensor 114 and flow controller 110 is signal line 116 for transmitting an output signal from flow sensor 114 as a second input signal to flow controller 110. Operably connected between control valve 118, which is interposed in conduit 79, and flow controller 110 is signal line 120 for transmitting an output signal from flow controller 110 to control valve 118.

For controlling the reflux flow rate to fractionator 12 is reflux flow control system 122. Provided in reflux flow control system 122 is flow sensor 124 for sensing the fluid flow rate passing through conduit 65. For transmitting an output signal from flow sensor 124 as a first input signal to flow controller 126 is signal line 128 that is operably connected between flow sensor 124 and flow controller 126. For transmitting a second input signal to flow controller 126 is signal line 130 that is operably connected between manual input signal switch 132 and flow controller 126. Operably connected between flow controller 126 and control valve 134, which is interposed in conduit 65, is signal line 136 for transmitting an output signal from controller 126 to control valve 134.

For controlling the pressure of stripping column 66 is pressure control system 138. Provided in pressure control system 138 is pressure sensor 140 for sensing the pressure in stripping column 66. For transmitting an output signal, which serves as a first input signal to pressure controller 142 from pressure sensor 140, is signal line 144 that is operably connected between pressure sensor 140 and pressure controller 142. For transmitting a second input to pressure controller 142 is signal line 146 that is operably connected between manual input signal switch 148 and pressure controller 142. Operably connected between pressure controller 142 and control valve 150, which is interposed in conduit 77, is signal line 152 for transmitting an output signal from pressure controller 142 to control valve 150.

For controlling the fluid flow rate to stripper column 66 is a flow control system 154. Provided in flow control system 154 is flow sensor 156, operably located in conduit 76, for sensing the flow rate of the fluid passing through conduit 76. For transmitting an output signal from flow sensor 156 as a first input signal to flow controller 158 is signal line 160 that is operably connected between flow sensor 156 and flow controller 158. For transmitting a second input signal to flow controller 158 is signal line 162 that is operably connected between flow controller 158 and manual input signal switch 164. Operably connected between flow controller 158 and control valve 166, which is interposed in conduit 76, is signal line 168 for transmitting an output signal from flow controller 158 to control valve 166.

For controlling the fluid level within stripping column 66 is level control system 170. Provided in level control system 170 is level sensor 172, which is operably connected to stripping column 66, for sensing the fluid level in stripping column 66. For transmitting an output signal from level sensor 172, which serves as a first input signal to level controller 174, is signal line 176, which is operably connected between level sensor 172 and level controller 174. For transmitting a second input signal to level controller 174 is signal line 178 that is operably connected between level controller 174 and manual input signal switch 180. Operably connected between level controller 174 and control valve 182, which is interposed in conduit 78, is signal line 184 for transmitting an output signal from level controller 174 to control valve 182.

For controlling the fluid level within fractionator 12 is level control system 186. Provided in level control system 186 is level sensor 188, which is operably connected to fractionator 12, for sensing the fluid level in fractionator 12. For transmitting an output signal from level sensor 188 as a first input signal to level controller 190 is signal line 192 that is operably connected between level sensor 188 and level controller 190. For transmitting a second input signal to level controller 190 is signal line 194 that is operably connected between level controller 190 and manual input signal switch 196. Operably connected between level controller 190 and control valve 198, which is interposed in conduit 25, is signal line 200 for transmitting an output signal from level controller 190 to control valve 198.

In operating propane stripping system 10 illustrated in FIG. 1, an HF alkylation reactor effluent having a concentration of HF acid is charged as a feed to fractionator 12 through conduit 24. The HF alkylation reactor effluent is the reaction product resulting from intimately mixing, under suitable alkylation conditions, olefins and isoparaffins with HF acid, which serves as a catalyst, to produce a high octane alkylate, unreacted isoparaffins, normal paraffins and light hydrocarbons. Fractionator 12 defines a separation zone and provides separation means for separating the HF alkylation reactor effluent or hydrocarbon product into a fractionator bottoms product comprising essentially butane and heavier hydrocarbons or alkylate and an overhead hydrocarbon fraction comprising essentially propane and lighter hydrocarbons. The fractionator bottoms product of fractionator 12, containing primarily alkylate and butane, passes through conduit 25 either to be charged to an isostripper (not shown) for the separation of alkylate and butane or to be recycled for mixing with olefin feed prior to entry into an alkylation reactor (not shown). The overhead hydrocarbon fraction from fractionator 12, containing a vapor mixture of substantially propane with small quantities of butanes and heavier hydrocarbons, ethanes and lighter hydrocarbons, and HF acid, passes by way of conduit 50 to condenser 28 wherein indirect heat exchange is accomplished to condense a significant portion of the overhead hydrocarbon fraction. Condenser 28 defines a condensation zone and provides means for condensing the overhead hydrocarbon fraction to produce a condensed hydrocarbon mixture. Condenser 28 can be any suitable type of heat exchange equipment and can use any form of heat exchange medium, but it is preferable that condenser 28 be of the shell-and-tube type exchanger and the heat transfer medium be cooling water. The condensed hydrocarbon mixture passes by way of conduit 52 to overhead accumulator 34 wherein a phase separation occurs between an HF acid phase, a hydrocarbon phase, and a non-condensible gaseous phase comprising primarily ethane, methane, and HF acid. Overhead accumulator 34, comprising top section 42, medial section 36, and bottom section 46, defines a top zone, a medial zone and a bottom zone, all three zones of which comprise a separation zone defined by overhead accumulator 34. Overhead accumulator 34 additionally provides means for receiving the condensed hydrocarbon mixture and for separating the condensed hydrocarbon mixture into at least two phases comprising an HF acid phase, which accumulates in the bottom zone, and a separated condensed hydrocarbon feed mixture phase, which accumulates in the medial zone. Optionally, a non-condensible gaseous phase can be separated within the separation zone defined by overhead accumulator 34 and accumulated within the top zone. The non-condensible gaseous phase can be removed from the top zone defined by top section 42 of overhead accumulator 34 by passing through conduit 54 for further downstream processing (not shown).

The accumulation of the HF acid phase in the bottom zone defined by bottoms section 46 of overhead accumulator 34 is removed by way of conduit 56. The level of the HF acid phase is measured by level sensor 84, which provides sensing means for sensing the HF acid level in bottom section 46 and which transmits a signal through signal line 88 to level controller 86 representative of the measured or actual level of the HF acid phase in bottoms section 46. Level controller 86 provides means for performing a comparison between a desired level, which is generally represented by a controller set point input signal imparted by means of manual input signal switch 92 and transmitted through signal line 90, and the measured level and establishes an output signal that is responsive to the difference between the measured level and the desired level and is transmitted through signal line 96. The output signal transmitted through signal line 96 is scaled to be representative of the position of level control valve 94 that provides control valve means for maintaining an HF acid flow through conduit 56 at a rate necessary to maintain the actual level of the HF acid phase in bottom section 46 substantially equal to the desired level represented by the controller set point input signal imparted by manual input signal switch 92.

The accumulation of the separated condensed hydrocarbon feed mixture phase in the medial zone defined by medial section 36 of overhead accumulator 34 is removed by way of conduit 64 and passes via conduit 64 to pump 60 that provides charging means for feeding the separated condensed hydrocarbon feed mixture phases to stripping column 66. Stripping column 66 defines a separation zone and provides means for separating the separated condensed hydrocarbon feed mixture phase, which is fed to stripping column 66 via conduit 76, into an overhead fraction and a bottoms fraction. The overhead fraction will generally be a gaseous mixture comprising at least a portion of the separated condensed hydrocarbon feed mixture phase that is fed to stripping column 66 and essentially all the HF acid contained in the separated condensed hydrocarbon feed mixture phase. The bottoms fraction will generally be a bottoms product comprising that remaining fraction of the separated condensed hydrocarbon feed mixture phase fed to stripping column 66 that is not a part of the overhead fraction.

Pump 60 can be any suitable mechanical device or means for imparting pressure head and velocity head to a fluid and for charging or feeding, via conduit 76, the separated condensed hydrocarbon feed mixture phase to stripping column 66 as a stripping column 66 feed stream. Additionally, pump 60 is utilized as means for optionally refluxing or returning at least a portion of the separated condensed hydrocarbon feed mixture phase to fractionator 12 as a reflux stream via conduit 65.

The flow rate of the stripping column 66 feed stream that is fed or charged to stripping column 66 via conduit 76 is controlled by flow control system 154, and the flow rate of the reflux stream refluxed to fractionator 12 via conduit 65 is controlled by reflux flow control system 122. The flow rate of the stripping column 66 feed stream is measured by flow sensor 156, which provides means for sensing and for measuring the actual flow rate of the stripping column 66 feed stream passing through conduit 76 and which transmits a signal through signal line 160 to flow controller 158 representative of the actual or measured flow rate through conduit 76. Flow controller 158 provides means for performing a comparison between a desired flow rate, which is generally represented by a controller set point input signal imparted by means of manual input signal switch 164 and transmitted through signal line 162, and the measured level and establishes an output signal, which is responsive to the difference between the measured level and the desired level, transmitted through signal line 168. The output signal transmitted through signal line 168 is scaled to be representative of the position of control valve 166 that provides control valve means for maintaining a stripping column 66 feed stream flow through conduit 76 at a rate necessary to maintain the actual flow rate substantially equal to the desired flow rate represented by the controller set point input signal imparted by manual input switch 164.

The flow rate of the reflux stream passing through conduit 65 is measured by flow sensor 124, which provides sensing means for sensing and for measuring the actual flow rate of the reflux stream and which transmits a signal through signal line 128 to flow controller 126 representative of the actual or measured flow rate through conduit 65. Flow controller 126 provides means for performing a comparison between a desired flow rate, which is generally represented by a controller set point input signal imparted by means of manual input signal switch 132 and transmitted through signal line 130, and the measured flow rate and establishes an output signal, which is responsive to the difference between the measured flow rate and the desired flow rate, transmitted through signal line 136. The output signal transmitted through signal line 136 is scaled to be representative of the position of the control valve 134 that provides control valve means for maintaining a reflux stream flow through conduit 65 at a rate necessary to maintain the actual flow rate subsequently equal to the desired flow rate represented by the controller set point input signal imparted by manual input switch 132.

The accumulation of bottoms product in the bottom of stripping column 66 is removed by way of conduit 78. The level of bottoms product in stripping column 66 is measured by level sensor 172, which provides sensing means for sensing the bottoms product level in stripping column 66 and which transmits a signal through signal line 176 to level controller 174 representative of the measured or actual level of the bottom product accumulated in stripper column 66. Level controller 174 provides means for performing a comparison between a desired level, which is generally represented by a controller set point input signal imparted by means of manual input signal switch 180 and transmitted through signal line 178, and the measured level and establishes an output signal, which is responsive to the difference between the measured level and the desired level, transmitted through signal line 184. The output signal transmitted through signal line 184 is scaled to be representative of the position of control valve 182, which provides control valve means for maintaining a bottoms product flow through conduit 78 at a rate necessary to maintain the actual level of bottoms product in stripping column 66 substantially equal to the desired level represented by the controller set point input signal imparted by manual input signal switch 92.

The pressure of stripping column 66 is controlled by pressure control system 138. The pressure of stripping column 66 is measured by pressure sensor 140, which provides means for sensing the pressure in stripping column 66 and which transmits a signal through signal line 144 to pressure controller 42 representative of the measured or actual pressure of stripper column 66. Pressure controller 142 provides means for performing a comparison between a desired pressure, which is generally represented by a controller set point input signal imparted by means of manual input signal switch 148 and transmitted through signal line 146, and the measured pressure and establishes an output signal, which is responsive to the difference between the measured pressure and the desired pressure, transmitted through signal line 152. The output signal transmitted through signal line 152 is scaled to be representative of the position of control valve 150, which provides means for maintaining the flow of the gaseous mixture through conduit 77 at a rate necessary to maintain the actual pressure of stripping column 66 substantially equal to the desired pressure represented by the controller set point input signal imparted by manual input signal switch 148.

The gaseous mixture flows from stripping column 66 by way of conduit 77 to condenser 28 where prior to entering condenser 28 it is mixed with the overhead hydrocarbon fraction from fractionator 12, which passes by way of conduit 50 to condenser 28. The thus-formed mixture of overhead hydrocarbon fraction and gaseous mixture passes through condenser 28 whereby an indirect heat exchange between the thus-formed mixture and a heat transfer fluid occurs in a manner to condense a significant portion of the thus-formed mixture. The resultant fluid passes by way of conduit 52 to overhead accumulator 34 wherein a phase separation occurs as hereinabove described.

The level of the separated condensed hydrocarbon feed mixture phase in medial section 36 is measured by level sensor 100, which provides sensing means for sensing the separated condensed hydrocarbon feed mixture phase in medial section 36 and which transmits a signal through signal line 104 to level controller 102 representative of the measured or actual level of the separated condensed hydrocarbon feed mixture phase accumulated in medial section 36. Level controller 102 provides means for performing a comparison between a desired level, which is generally represented by a controller set point input signal imparted by means of manual input signal switch 108 and transmitted through signal line 106, and the measured level and establishes an output signal, which is responsive to the difference between the measured level and the desired level, transmitted through signal line 106. The output signal transmitted through signal line 112 is scaled to be representative of the position of control valve 118, which provides means for maintaining a fluid flow through conduit 79 at a rate necessary to maintain the actual level in medial section 36 substantially equal to the desired level as represented by the controller set point input signal imparted by manual input signal switch 108.

The accumulation of fractionator bottoms product of fractionator 12 is removed by way of conduit 25. The level of fractionator bottoms product in fractionator 12 is measured by level sensor 188, which provides sensing means for sensing the fractionator bottoms product level in fractionator 12 and which transmits a signal through signal line 192 to level controller 190 representative of the measured or actual level of the fractionator bottoms product accumulated in fractionator 12.

Level controller 190 provides means for performing a comparison between a desired level, which is generally represented by a controller set point input signal imparted by means of manual input signal switch 196 and transmitted through signal line 194, and the measured level and establishes an output signal, which is responsive to the difference between the measured level and the desired level, transmitted through signal line 200. The output signal transmitted through signal line 200 is scaled to be representative of the position of control valve 198, which provides control valve means for maintaining a fractionator bottoms product flow through conduit 25 at a rate necessary to maintain the actual level of fractionator bottoms product in fractionator 12 substantially equal to the desired level represented by the controller set point input signal imparted by manual input signal switch 196.

In summary, with respect to the propane stripping system 10 illustrated in FIG. 1, process equipment and control elements are ranged in a manner such that a propane stripper contained within an HF alkylation system can be easily controlled during wide variations of propane stripper charge rates to provide a propane product essentially free of HF acid. This is a particularly desired feature of the present invention.

The invention has been described in terms of a preferred embodiment as illustrated in FIG. 1. Specific components used in the practice of the invention as illustrated in FIG. 1 such as flow sensors, level sensors, pressure sensors, controllers, and control valves are each well known, commercially available control components such as described at length in Perry's *Chemical Engineers Handbook*, 6th Edition, Chapter 22, McGraw-Hill.

While specific materials, conditions of operation, modes of operation and equipment have been referred herein, it is to be recognized that these and other specific recitals are for illustrative purposes and to set forth the best mode only and are not to be considered limiting.

That which is claimed is:

1. An apparatus used in an HF alkylation process for the removal of HF acid from a hydrocarbon product comprising:

a fractionator having a feed inlet, an overhead outlet, a bottoms outlet and a reflux inlet;

first conduit means operably connected to said bottoms outlet, for conveying fractionator bottoms product from said fractionator;

second conduit means operably connected to said feed inlet;

condenser means, having a condenser inlet and a condenser outlet;

third conduit means operably connected between said overhead outlet and said condenser inlet;

an overhead accumulator, having a top section, a medial section, a bottom section, an inlet, a first outlet in fluid flow communication with said medial section, a second outlet in fluid flow communication with said bottom section and a third outlet in fluid flow communication with said top section;

fourth conduit means operably connected between said condenser outlet and said inlet of said overhead accumulator;

a stripping column having a stripper inlet, a stripper overhead outlet and a stripper bottoms outlet;

charging means, having a suction inlet and a discharge outlet;

fifth conduit means operably connected between said first outlet of said accumulator and said section inlet of said charging means;

sixth conduit means operably connected between said discharge outlet of said charging means and said stripper inlet;

seventh conduit means operably connected between said stripper overhead outlet and said condenser inlet;

eighth conduit means operably connected to said stripper bottoms outlet, for conveying stripper bottoms product from said stripping column;

ninth conduit means operably connected between said eighth conduit means and said suction inlet of said charging means;

tenth conduit means operably connected to said second outlet of said accumulator, for conveying HF acid phase from said overhead accumulator; and eleventh conduit means operably connected to said third outlet of said accumulator, for conveying ethane and lighter gases from said overhead accumulator.

2. An apparatus according to claim 1, further including:

means, operably connected to said medial section, for establishing a first signal representative of an actual level in said medial section;

means for establishing a second signal representative of a predetermined level in said medial section;

means for comparing said first signal and said second signal and establishing a third signal responsive to the difference between said first signal and said second signal wherein said third signal is scaled to be representative of a flow rate of said at least a portion of said stripping column bottoms product required to maintain the actual level in said medial section, represented by said first signal, substantially equal to the predetermined level represented by said second signal;

means, operably located in said ninth conduit means, for establishing a fourth signal representative of the actual flow rate of said at least a portion of said stripping column bottoms product;

means for comparing said fourth signal and said third signal and for establishing a fifth signal responsive to the difference between said third signal and said fourth signal wherein said fifth signal is scaled to be representative of the flow rate of said at least a portion of said stripping column bottoms product required to maintain the actual level in said medial section, represented by said first signal, substantially equal to the predetermined level represented by said second signal; and control valve means, interposed in said ninth conduit means, for manipulating a flow rate of said at least a portion of said stripping column bottoms product in response to said fifth signal.

3. An apparatus according to claim 2, further including:

means, operably connected to said stripping column, for establishing a sixth signal representative of an actual level in said stripping column;

means for establishing a seventh signal representative of a predetermined level in said stripping column;

means for comparing said sixth signal and said seventh signal and establishing an eighth signal responsive to the difference between said sixth signal and said seventh signal wherein said eighth signal is scaled to be representative of a flow rate of said stripping column bottoms product required to maintain the actual level in said stripping column, represented by said sixth signal, substantially equal to the predetermined level represented by said seventh signal;

control valve means, interposed in said eighth conduit means, for manipulating the flow rate of said stripping column bottoms product in response to said eighth signal.

4. An apparatus according to claim 3, further including:

means, operably located in said seventh conduit means, for establishing a ninth signal representative of an actual pressure in said stripping column;

means for establishing a tenth signal representative of a predetermined pressure in said stripping column;

means for comparing said ninth signal and said tenth signal and establishing an eleventh signal responsive to the difference between said ninth signal and said tenth signal wherein said eleventh signal is scaled to be representative of a flow rate of said overhead stream required to maintain the actual pressure in said stripping column, as represented by said ninth signal, substantially equal to the predetermined pressure in said stripping column represented by said tenth signal; and control valve means, interposed in said seventh conduit means, for manipulating the flow rate of said overhead stream in response to said eleventh signal.

5. An apparatus according to claim 4, further including:

means, operably connected to said bottom section, for establishing a twelfth signal representative of an actual level of said HF acid phase in said bottom section;

means for establishing a thirteenth signal representative of a predetermined level of HF acid phase in said bottom section;

means for comparing said twelfth signal and said thirteenth signal and establishing a fourteenth signal responsive to the difference between said twelfth signal and said thirteenth signal wherein said fourteenth signal is scaled to be representative of a flow rate of said HF acid phase required to maintain the actual level in said bottom section, represented by said twelfth signal, substantially equal to the predetermined level represented by said thirteenth signal; and control valve means, interposed in said tenth conduit means, for manipulating the flow rate of said HF acid phase in response to said fourteenth signal.

6. An apparatus according to claim 5, further including:

twelfth conduit means operably connected between said discharge outlet of said charging means and said reflux inlet of said fractionator.

7. An apparatus according to claim 6, further including:

means, operably located in said twelfth conduit means, for establishing a fifteenth signal representative of an actual flow rate of said reflux;

means for establishing a sixteenth signal representative of a predetermined flow rate of said reflux;

means for comparing said fifteenth signal and said sixteenth signal and establishing a seventeenth signal responsive to the difference between said fifteenth signal and said sixteenth signal wherein said seventeenth signal is scaled to be representative of a flow rate of said reflux required to maintain the actual flow rate, as represented by said fifteenth signal, substantially equal to the predetermined flow rate of said reflux as represented by said sixteenth signal; and control valve means, interposed in said twelfth conduit means, for manipulating the flow rate of said reflux in response to said seventeenth signal.

8. An apparatus according to claim 7, further including:

means, operably connected to said fractionator, for establishing an eighteenth signal representative of an actual level in said fractionator;

means for establishing a nineteenth signal representative of a predetermined level in said fractionator;

means for comparing said eighteenth signal and said nineteenth signal and establishing a twentieth signal responsive to the difference between said eighteenth signal and said nineteenth signal wherein said twentieth signal is scaled to be representative of a flow rate of said fractionator bottoms product required to maintain the actual level in said fractionator, represented by said eighteenth signal, substantially equal to the predetermined level in said fractionator represented by said nineteenth signal; and control valve means interposed in said first conduit means for manipulating the flow rate of said fractionator bottoms product in response to said twentieth signal.

* * * * *